United States Patent [19]

McDow

[11] Patent Number: 5,330,745

[45] Date of Patent: * Jul. 19, 1994

[54] METHOD FOR USING CRYOGENIC AGENTS FOR TREATING SKIN LESIONS

[76] Inventor: Ronald A. McDow, 1717 Nottingham Pl., Nashville, Tenn. 37221

[*] Notice: The portion of the term of this patent subsequent to Apr. 6, 2010 has been disclaimed.

[21] Appl. No.: 4,119

[22] Filed: Jan. 13, 1993

Related U.S. Application Data

[63] Continuation-in-part of Ser. No. 381,296, Jul. 18, 1989, Pat. No. 5,200,170.

[51] Int. Cl.$^5$ .................. A61K 9/08; A61L 9/04; A61M 35/00; A01N 25/02
[52] U.S. Cl. .................................. 424/45; 424/43; 604/49; 604/289; 604/290; 604/291
[58] Field of Search ............ 424/45, 43, 47; 128/DIG. 27, 399, 400, 402, 403; 604/49, 291, 289, 290

[56] References Cited

U.S. PATENT DOCUMENTS 5,127,395  7/1992  Bontemps .......................... 128/24.3

Primary Examiner—Thurman K. Page
Assistant Examiner—Carlos Azpuru
Attorney, Agent, or Firm—Parmelee, Bollinger & Bramblett

[57] ABSTRACT

A method for cryogenically treating skin lesions employing a hollow fluid retaining device for retaining cryogenic refrigerant in a liquid pool contacting the area of the skin lesion at a temperature and for a time such that permanent, irreversible rupture of the cellular membrane of the skin cells occurs.

20 Claims, 1 Drawing Sheet

METHOD FOR USING CRYOGENIC AGENTS FOR TREATING SKIN LESIONS

RELATED APPLICATIONS

This application is a continuation-in-part of allowed U.S. patent application Ser. No. 07/381,296, filed Jul. 18, 1989, now U.S. Pat. No. 5,200,170.

FIELD OF THE INVENTION

This invention relates to the field of cryogenic surgery for skin lesions and mucous membranes, including vaginal and cervical lesions and to an improved method for conducting said cryosurgery with various cryogenic agents.

BACKGROUND OF THE INVENTION

Conventional methods of treatment of skin lesions have generally employed conventional surgical methods or a cryogenic method employing liquid nitrogen. Currently, methods used are scalpel (cold steel) surgery, electrodesiccation, and use of liquid nitrogen in cryogenic methods. However, there are a number of significant drawbacks and problems associated with these prior art methods, including, among other things, undue cost, excess time required, complications and the need for expensive storage dewars.

Among the problems associated with the use of liquid nitrogen as a cryogenic agent in heretofore employed cryogenic procedures are (1) a 3–5% evaporation of the liquid nitrogen product while being stored for use, (2) the need for expensive storage dewars for liquid nitrogen generally costing from about $600 to about $2500, (3) expensive delivery systems generally costing from about $700 to about $3000 generally required to spray this cryogen into skin and mucous membranes, and (4) occasional permanent hypopigmentation and hypertrophic scarring.

These drawbacks and problems have adversely affected the number of physicians able to perform such operations and the number of patients to receive such treatments for skin lesions.

Among the problems associated with scalpel (cold steel) surgery are (1) bacterial skin infection rates of up to about 18% depending upon, among other things, the sterile technique employed by the operator and heat and humidity of the location of the surgery, (2) hypertrophic scarring which can occur in up to about 25% of patients depending, in general, upon the operator's skill, experience and judgement, and the patient's genetic predisposition to scar, and (3) inefficient use of time. Most scalpel surgery procedures generally require about 25 to 50 minutes to perform. This time is necessitated by the time required for (a) anaesthetizing the treatment area, (b) about 5 minutes waiting period for lidocaine to become optimally effective, (c) time for preparing a sterile operating field, and (d) time for performing the scalpel surgery procedure.

Among the problems associated with electrodesiccation are (1) time consuming need for a local anaesthetic to be applied and become optimally effective and (2) permanent hypertrophic scarring that occurs in a significant percentage of patients undergoing this procedure.

An example of the literature discussing some of these prior art methods and corresponding problems is *Skin Surgery*, Irwin Epstein and Irwin Epstein, Jr., 6th edition, 1987, W. B. Saunders, Philadelphia, Pa., pages 180–182 which includes pictures of facial hypertrophic scarring following curettage and electrodesiccation.

It is therefore an object of this invention to provide an improved method for the treatment of skin lesions that substantially eliminates or avoids the aforesaid drawbacks and problems. A further object of this invention is to produce such a method for treating skin lesions which will be less expensive than procedures heretofore used and thus allow more physicians to perform and patients to receive such treatment at much less cost, and which requires less time involved in the procedure and with less side effects or complications, such as infections, hypertrophic scarring and the like. A still further object of this invention is to provide such an improved method for treatment of skin lesions which does not require expensive storage dewars and no need for expensive delivery devices. An even still further object of this invention is to provide such an improved method for treatment of skin lesions requiring up to or about 1/15th of the time required for traditional scalpel surgery or electrodesiccation and curettage which most physicians currently use to treat such skin lesions. A yet still further object is to provide an improved method for treatment of skin lesions in which the potential for human suffering and permanent disfigurement is substantially eliminated or avoided. Additionally, an object of this invention is to provide an improved process for treatment of skin lesions which is more time-efficient and thus saves physician and patient time involved in the procedure. Another additional object of this invention is to provide an improved method for treatment of skin lesions having significant economical and cosmetic benefit to physicians and patients, and which is portable, i.e. is capable of easily being carried from office to office or office to hospital.

BRIEF DESCRIPTION OF THE DRAWINGS

This invention is to be understood in connection with the drawings which illustrate examples of apparatus and devices suitable for use in carrying out the method of this invention.

BRIEF DESCRIPTION OF THE INVENTION

Figure 1:
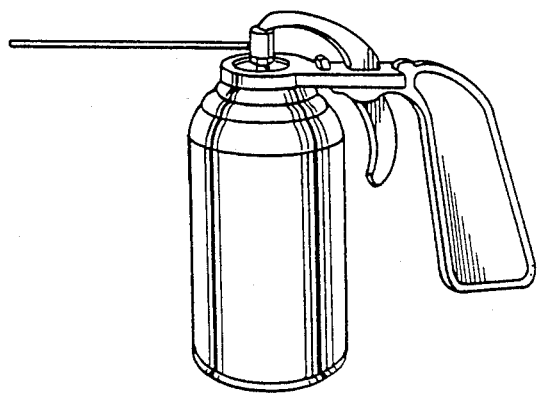
FIG. 1 discloses apparatus for use in the introducing cryogenic agent in the treatment method of this invention.

The method for treatment of skin lesions of this invention comprises a method for cryogenic treatment of skin lesions which permits the use of such method with a wide variety of refrigerants as cryogenic agents. The method of this invention comprises (a) placing a hollow fluid retaining device, having a side wall defining a bottom open end of a size at least slightly greater than a skin lesion to be treated and a top open end, in an essentially upright position on a patient's skin in a manner whereby the bottom open end seals against a patient's skin entirely surrounding the skin lesion and the top open end is above the bottom open end, (b) introducing into the top open end of the essentially upright fluid retaining device a liquid cryogenic agent to cause formation of a liquid pool of the cryogenic agent to contact directly the entire area of the skin lesion, (c) terminating the introduction of the cryogenic agent, (d) retaining the hollow fluid retaining device in the essentially upright position surrounding the skin lesion, after the introduction step has terminated, in order to retain the liquid pool of cryogenic agent within the bottom open end of the fluid retaining device and in contact directly with the entire area of the skin lesion for a period of time to permit the cryogenic agent to reduce the temperature of the skin lesion to a temperature such that permanent, irreversible rupture of cellular membranes of cells of the skin lesion occurs while the cryogenic agent is evaporating, and (e) subsequently removing the fluid retaining device from its essentially upright position after the liquid cryogenic agent has evaporated. After the cryogenic agent has evaporated, the frozen skin tissue of the skin lesion is permitted to slowly thaw, preferably over a period of time that is at least about 45 to 65 seconds.

This cryogenic method for treatment of skin lesions is believed to be highly effective due to the freeze-thaw cycle that occurs on the skin tissue and the vascular stasis (microcirculatory failure) which develops in the tissue after thawing. The freezing of the skin lesion cells causes intracellular crystallization of water, concentration of solute in the cells, and irreversible changes in the cell membranes. The vascular stasis leads to a loss of blood supply and thus essentially deprives the cells of the skin lesion any possibility of survival.

The method of this invention employs as liquid cryogenic agent any suitable liquid cryogenic agent capable of providing reduced skin temperatures suitable for producing such permanent, irreversible rupture of cellular membranes of cells of the skin lesions when said cryogenic agent is placed on a skin lesion of a patient in accordance with the method of this invention. It is believed that a liquid cryogenic agent reducing the temperature of the skin to a temperature which is no higher than −20° C., preferably no higher than about −30° C., is suitable for use in the method of this invention. As examples of preferred cryogenic agents suitable for use in the method of this invention there can be mentioned such cryogenic agents as chlorodifluoromethane ($CHClF_2$), dichlorodifluoromethane ($CCl_2F_2$), trifluoromethane ($CHF_3$), 2,2-difluoro-1,1,1-trifluoroethane ($CHCl_2CF_3$), 2-chloro-1,1,1,2-tetrafluoroethane ($CHClFCF_3$), 1,1,1,2,2-pentafluoroethane ($CHF_2CF_3$), 1,1,1,2-tetrafluoroethane ($CH_2FCF_3$), 1,1-dichloro-1-fluoroethane ($CH_3CCl_2F$), 1-chloro-1,1-difluoroethane ($CH_3CClF_2$), and 1,1-difluoroethane ($CH_3CHF_2$). Since these cryogenic agents evidence essentially no evaporation on storage, no need for expensive storage dewars or expensive delivery devices the method of this invention can be up to 1/100 of the cost of using liquid nitrogen to treat skin lesions and this is an extremely practical medical advance. Also suitable as cryogenic agents for use in the method of this invention there may be mentioned for example, methane, propane, isobutane, n-butane and dimethyl ether.

Suitable mixtures of the aforementioned suitable cryogenic agents may also be employed.

DETAILED DESCRIPTION OF THE INVENTION

The methodology of this invention for use with dichlorodifluoromethane and chlorodifluoromethane has been reviewed and approved by the U.S. Food and Drug Administration (FDA) from evidence that I have submitted to the FDA in confidence.

The use of the cryogenic agents in accordance with the method of this invention will generally reduce the skin temperature of the cells of the skin lesion to a temperature which is no higher than about −20° C., preferably no higher than about −30° C., and even more preferably no higher than about −50° C. In general the method of treatment in accordance with this invention will generally produce a ⅛″ to ¼″ pool of liquid cryogenic agent on the skin lesion and thereby reduce the temperature to a skin temperature within the range of from about −30° C. to about −120° C. in order to cause suitable destruction (necrosis) of the cells of the of the skin lesion.

Rapid freezing of the cells promotes increased cellular destruction. Also, slow, unassisted thawing which lasts at least about 45 to 65 seconds increases cellular destruction. Thus, suitable cryogenic agents with longer thaw times, generally from about 45 to 65 seconds or longer, are generally preferred. The ability of suitable cryogenic agents to be effectively employed in the method of this invention thus, in part, resides in their ability to freeze rapidly the cells of the skin lesions and then thaw slowly which is believed to be a function, at least in part, of both the boiling point of the cryogenic agent and its latent heat of vaporization. For example, although the boiling point of dichlorodifluoromethane is −29.8° C. actual freezing temperatures as low as −60° C. using cryoprobes have been recorded.

Although many skin lesions may be suitably treated and removed by the five steps (a) through (e) of the method set forth in the hereinbefore Brief Description of the Invention section of this Application, it is often desirable and highly beneficial to permit the skin lesion to thaw completely after removing the fluid retaining device and to sequentially repeat steps (a) through (e). Such repetition of freeze-thaw cycles promotes increased cellular destruction and thus improved removal of skin lesions.

Although the suitable length of time employed for introducing or spraying the cryogenic agent into the hollow fluid retaining device can vary widely depending, at least in part, upon the type of skin lesion, its size and thickness, it has been found that a period of from about 3 to 10 seconds is generally suitable for epithelial skin lesions that are benign. Cryogenic agent is pooled on the skin lesion in the fluid retaining device and freezes skin cells. Usually freezing of the cryogenic agent continues for about 10 to about 25 seconds after spraying of the cryogenic agent has been discontinued. The total freezing time is generally about 20 to about 40 seconds.

After evaporation of the cryogenic agent the freezing is completed and the skin lesions are frozen and appear white. This signals the beginning of the thaw stage which generally amounts to a period of about 45 to about 65, preferably about 55 to 60 seconds.

The method of this invention is suitable for use in treating a wide variety of skin lesions and mucous membranes, including vaginal and cervical lesions, particularly verruca and seborrheic keratoses. Among the many skin lesions that may be treated according to the method of this invention there may be mentioned, for example, melanocytes, osteocytes, lentigo (age spots), seborrheic keratoses, actinic keratoses, achrochordon, molluscum contagiosum, verruca digitata lesions, verruca periungual lesions, verruca filiformis lesions, verruca glabra lesions, verruca plana lesions, verruca plantaris lesions, verruca vulgaris lesions, and venereal warts.

Figure 2:
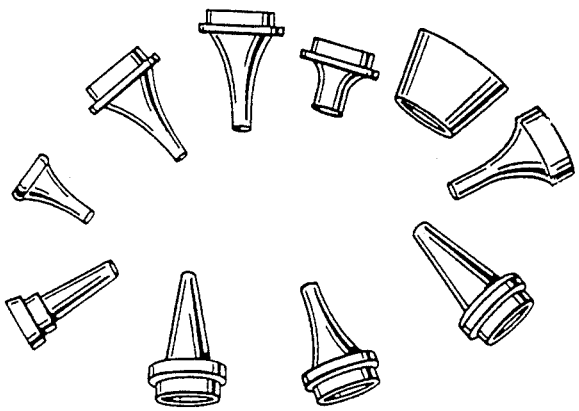
FIG. 2 discloses fluid retaining or fluid constricting devices for use in the treatment method of this invention to contain the spray of liquid cryogenic agent.

The method of this invention is illustrated but not limited by reference to the figures in the drawings. As an example of the best ways of carrying out the operation of the method of this invention, FIG. 1 discloses a cryogenic agent packaged in a can, preferably a 12 or 16 ounce can and dispensed through an aerosol nozzle. A capillary tube, preferably a 1 mm capillary tube, is attached to the aerosol nozzle to direct spray accurately into hollow fluid retaining or constricting devices which are illustrated in FIG. 2. The can may also be provided with a snap-on handle and trigger device as illustrated in FIG. 1 for ease of operation in dispensing cryogenic agent from the can into a retaining device in a manner that permits an appropriate amount of cryogenic agent to be dispensed while protecting the physician's hands and fingers from freezing.

In FIG. 2 there is illustrated a variety of hollow fluid retaining or constricting devices which are used to pool the liquid cryogenic agent and to limit the spread of the freeze. An appropriate size diameter top or opening of the fluid retaining device should be chosen to substantially match the size of the lesion to be treated and frozen. These fluid retaining devices may be neoprene cones or commonly available otoscopic cones, with or without a flexible tip for better seal, or hard substances capable of withstanding repeated freezing temperatures.

Figure 3:
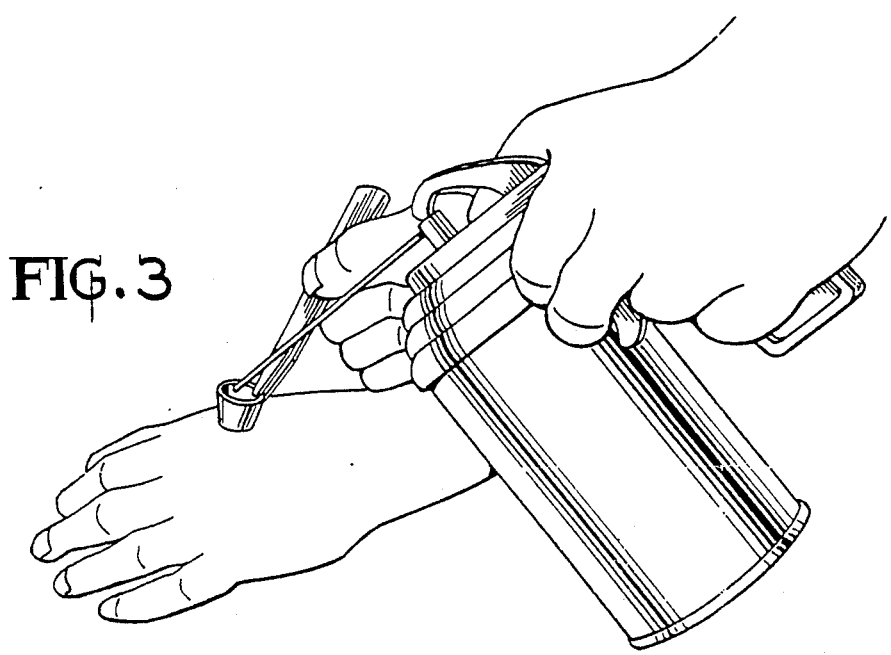
FIG. 3 demonstrates the treatment method of this invention.

FIG. 3 demonstrates the use of the apparatus to perform the method of this invention. The cryogenic agent is sprayed from the can through the capillary tube into the fluid retaining device held in a substantially upright position on a patient's skin in a manner to seal against the patient's skin around the skin lesion in the manner described in steps (a) through (e) of the method set forth in the hereinbefore Brief Description of the Invention section of this Application.

The method of this invention is further illustrated by the following examples.

EXAMPLE 1

Dichlorodifluoromethane ($CCl_2F_2$) is sprayed from 12 to 16 ounce aerosol cans through a one millimeter capillary applicator tube measuring 13 cm in length. This applicator tube is held 5 cm from the lesion being treated. This distance may vary approximately 2 cm to 3 cm each way. Through this procedure the spray is concentrated more precisely to the area being treated. The spray is focused into an appropriate sized fluid retaining or constricting device which surrounds the lesion being treated. About 3 to 10 seconds direct freeze application is used on most benign lesions. The duration of spray can be varied according to the size and thickness of the lesion. The dichlorodifluoromethane does not evaporate immediately after contacting the skin but rather accumulates within the cones or fluid retaining or constricting devices and continues to freeze about 10 to 25 seconds after the spraying ceases. After evaporation is complete, lesions being treated turn white. This represents the beginning of the thaw stage which averages about 45 to 65 seconds. Extreme care must be taken not to touch the lesions during this thaw stage. The heat from a finger or other body part would decrease the thaw time and diminish the cellular destructive potential of the cryogen. A second and third freeze-thaw cycle may be performed depending upon the thickness and width of the lesion being treated. Lidocaine may be used as a local anaesthetic prior to freezing in extremely sensitive patients but it is usually not necessary. Postoperative care includes leaving the lesion exposed to air unless a drainage develops, cleaning the lesion with peroxide daily, and allowing the ensuing crust formation to spontaneously detach.

Similar treatment methods can be performed using chlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and suitable mixtures of such cryogenic agents.

EXAMPLE 2

Evidence of the effectiveness of this methodology of the invention was established by treating in the hereinbefore described manner a total of 75 verruca lesions. Verruca lesions in the study included 33 verruca digitata and periungual lesions, 11 verruca plana lesions, and 31 verruca vulgaris lesions.

Expected erythema occurred. It was noted that the erythema occurred between one and two hours after freezing. Bulla formation was seen in the patients within one to two days. Sloughing of the lesions occurred between 5 and 12 days. Complete healing usually resulted within 18 days. Of the 75 verruca treated, 67 showed complete destruction and no recurrence at six months. Six showed incomplete sloughing after one freezing but cleared after a second treatment with no recurrence at six months. Two lesions showed recurrence within six months but cleared after treatment.

No complications occurred, and rapid healing progressed with some slight temporary hypopigmentation in some patients. The minimal discomfort experienced by patients during treatment varied among patients according to the pain threshold of each.

With the foregoing description of the invention, those skilled in the art will appreciate that modifications may be made to the invention without departing from the spirit thereof. Therefore, it is not intended that the scope of the invention be limited to the specific embodiments illustrated and described.

I claim:
1. A method of cryogenically treating a skin lesion comprising the steps of:
 (a) placing a hollow fluid retaining device, having a side wall defining a bottom open end of a size slightly greater than a skin lesion to be removed by cryosurgery and a top open end, in an essentially upright position on a patient's skin in a manner whereby said bottom open end seals against the patient's skin entirely surrounding said skin lesion and said top open end is above said bottom open end,
 (b) introducing into said top open end of said upright fluid retaining device a liquid cryogenic agent to cause formation of a liquid pool of said cryogenic agent to contact directly the entire area of said skin lesion,
 (c) terminating said introducing of said cryogenic agent step,
 (d) retaining said hollow fluid retaining device in said upright position surrounding said skin lesion after said introducing step has been terminated in order to retain said liquid pool of cryogenic agent within said bottom open end of said fluid retaining device and in contact directly with said skin lesion for a period of time to permit said cryogenic agent to reduce the temperature of said skin lesion to a temperature such that permanent, irreversible rupture of cellular membranes of cells of said skin lesion occurs while said cryogenic agent is evaporating, and (e) subsequently removing said fluid retaining device from said upright position after said liquid cryogenic agent has evaporated.

2. The method according to claim 1 further comprising the step of permitting said skin lesion to completely thaw after said step of removing said fluid retaining device, and sequentially repeating said steps of (a), (b), (c), (d) and (e).

3. The method according to claim 1 in which said period of time for said introducing step is about 3 to 10 seconds when said skin lesion is benign.

4. The method according to claim 1 in which said step of retaining said hollow fluid retaining device in said essentially upright position continues for a time period of about 10 to 25 seconds.

5. The method according to claim 2 in which the step of permitting the skin lesion to completely thaw occurs over a period of time of at least about 45 seconds.

6. A method of cryogenically treating a benign skin lesion comprising the steps of:

(a) placing a hollow fluid retaining device, having a side wall defining a bottom open end of a size slightly greater than a skin lesion to be removed by cryosurgery and a top open end, in an essentially upright position on a patient's skin in a manner whereby said bottom open end seals against the patient's skin entirely surrounding said skin lesion and said top open end is above said bottom open end, (b) introducing into said top open end of said upright fluid retaining device for a period of about 3 to 10 seconds a liquid cryogenic agent to cause formation of a liquid pool of said cryogenic agent to contact directly the entire area of said skin lesion, (c) terminating said introducing of said cryogenic agent step, (d) retaining said hollow fluid retaining device in said upright position surrounding said skin lesion for a period of about 10 to 25 seconds after said introducing step has been terminated in order to retain said liquid pool of cryogenic agent within said bottom open end of said fluid retaining device and in contact directly with said skin lesion for a period of time to permit said cryogenic agent to reduce the temperature of said skin lesion to a temperature such that permanent, irreversible rupture of cellular membranes of cells of said skin lesion occurs while said cryogenic agent is evaporating, (e) subsequently removing said fluid retaining device from said upright position after said liquid cryogenic agent has evaporated, and (f) permitting said skin lesion to completely thaw over a period of about 45 to 65 seconds after said step of removing said fluid retaining device, and sequentially repeating said steps of (a), (b), (c), (d) and (e).

7. The method of claim 1 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and mixtures of such cryogenic agents.

8. The method of claim 2 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and mixtures of such cryogenic agents.

9. The method of claim 3 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and mixtures of such cryogenic agents.

10. The method of claim 4 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and mixtures of such cryogenic agents.

11. The method of claim 5 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and mixtures of such cryogenic agents.

12. The method of claim 6 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and mixtures of such cryogenic agents.

13. The method of claim 1 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane and 1,1-difluoroethane.

14. The method of claim 2 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane and 1,1-difluoroethane.

15. The method of claim 3 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane and 1,1-difluoroethane.

16. The method of claim 4 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane and 1,1-difluoroethane.

17. The method of claim 5 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane and 1,1-difluoroethane.

18. The method of claim 6 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane and 1,1-difluoroethane.

19. The method of claim 12 wherein the skin lesion being treated is a lesion selected from the group consisting of melanocytes, osteocytes, lentigo, seborrheic keratoses, actinic keratoses, achrochordon, molluscum contagiosum, verruca digitata lesions, verruca periungual lesions, verruca filiformis lesions, verruca glabra lesions, verruca plana lesions, verruca plantaris lesions, verruca vulgaris lesions, and venereal warts.

20. The method of claim 18 wherein the skin lesion being treated is a lesion selected from the group consisting of melanocytes, osteocytes, lentigo, seborrheic keratoses, actinic keratoses, achrochordon, molluscum contagiosum, verruca digitata lesions, verruca periungual lesions, verruca filiformis lesions, verruca glabra lesions, verruca plana lesions, verruca plantaris lesions, verruca vulgaris lesions, and venereal warts.

* * * * *